United States Patent [19]
Sauter

[11] Patent Number: 5,891,055
[45] Date of Patent: Apr. 6, 1999

[54] GUIDE WIRE

[75] Inventor: Herbert Sauter, Winkel-Rüti, Switzerland

[73] Assignee: Schneider (Europe) A.G., Bulach, Switzerland

[21] Appl. No.: 295,976

[22] Filed: Aug. 25, 1994

Related U.S. Application Data

[63] Continuation of Ser. No. 207,576, Mar. 7, 1994, Pat. No. 5,429,139.

[30] Foreign Application Priority Data

May 19, 1993 [EP] European Pat. Off. .............. 93810371

[51] Int. Cl.$^6$ ..................................................... A61B 5/00
[52] U.S. Cl. ........................................... 600/585; 604/170
[58] Field of Search ..................... 128/657, 772; 604/164, 166, 170, 280, 282

[56] References Cited

U.S. PATENT DOCUMENTS

| Re. 33,911 | 5/1992 | Samson et al. | 128/772 |
|---|---|---|---|
| 4,538,622 | 9/1985 | Samson et al. | 128/772 |
| 4,545,390 | 10/1985 | Leary | 128/772 |
| 4,554,929 | 11/1985 | Samson et al. | 128/772 |
| 4,676,249 | 6/1987 | Arenas et al. | 128/772 X |
| 4,721,117 | 1/1988 | Mar et al. | 128/772 |
| 4,748,986 | 6/1988 | Morrison et al. | 128/772 |
| 4,757,827 | 7/1988 | Buchbinder et al. | 128/772 |
| 4,763,647 | 8/1988 | Gambale | 128/657 |
| 4,922,924 | 5/1990 | Gamble et al. | 128/772 |
| 4,966,163 | 10/1990 | Kraus et al. | 128/772 |
| 5,063,935 | 11/1991 | Gambale | 128/657 |
| 5,067,489 | 11/1991 | Lind | 128/772 |
| 5,084,022 | 1/1992 | Claude | 128/772 X |
| 5,109,867 | 5/1992 | Twyford, Jr. | 128/772 |
| 5,114,959 | 9/1992 | Gambale et al. | 128/657 X |
| 5,131,406 | 7/1992 | Kaltenbach | 128/657 |
| 5,147,317 | 9/1992 | Shank et al. | 604/164 |
| 5,174,302 | 12/1992 | Palmer | 128/772 |
| 5,197,486 | 3/1993 | Frassica | 128/657 X |
| 5,228,453 | 7/1993 | Sepetica | 128/657 X |
| 5,259,393 | 11/1993 | Corso, Jr. et al. | 128/772 |
| 5,271,415 | 12/1993 | Foerster | 128/772 |

FOREIGN PATENT DOCUMENTS

| 0318046 | 5/1989 | European Pat. Off. . |
|---|---|---|
| 0419277 | 3/1991 | European Pat. Off. . |
| 9204072 | 3/1992 | WIPO . |
| 9219151 | 11/1992 | WIPO . |
| 9524237 | 9/1995 | WIPO . |

*Primary Examiner*—Michael A. Brown
*Attorney, Agent, or Firm*—Peter C. Richardson; Lawrence C. Akers; Philip C. Strassburger

[57] ABSTRACT

The guide wire of this invention is especially suited for the percutaneous introduction of a balloon dilatation catheter into a blood vessel. It contains a flexible shaft with a proximal portion and a distal portion. A flexible helical coil assembly surrounds the distal portion of the shaft. The helical coil assembly has a radiographically visible distal helical coil and a proximal radiographically invisible helical coil. The proximal helical coil and the distal helical coil are attached to each other by a connecting helical coil that on one end is screwed into the proximal helical coil and on the other end is screwed into the distal helical coil.

26 Claims, 6 Drawing Sheets

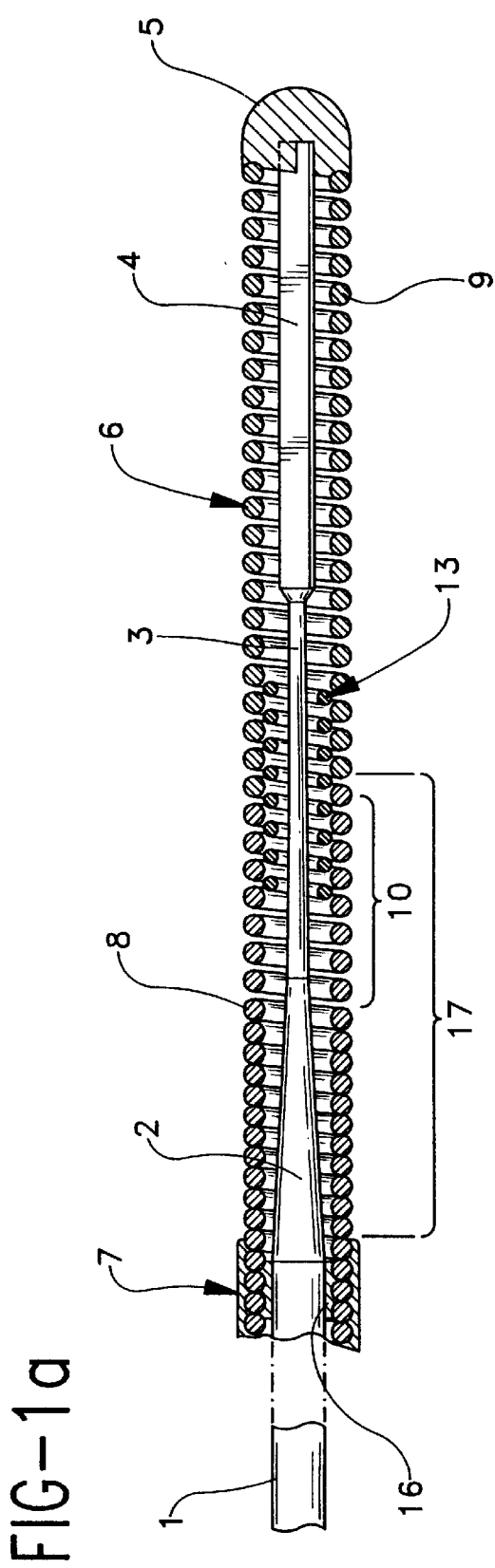
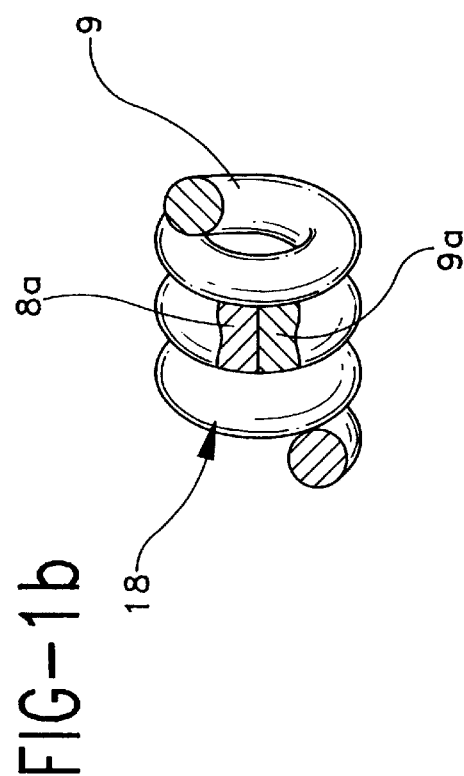

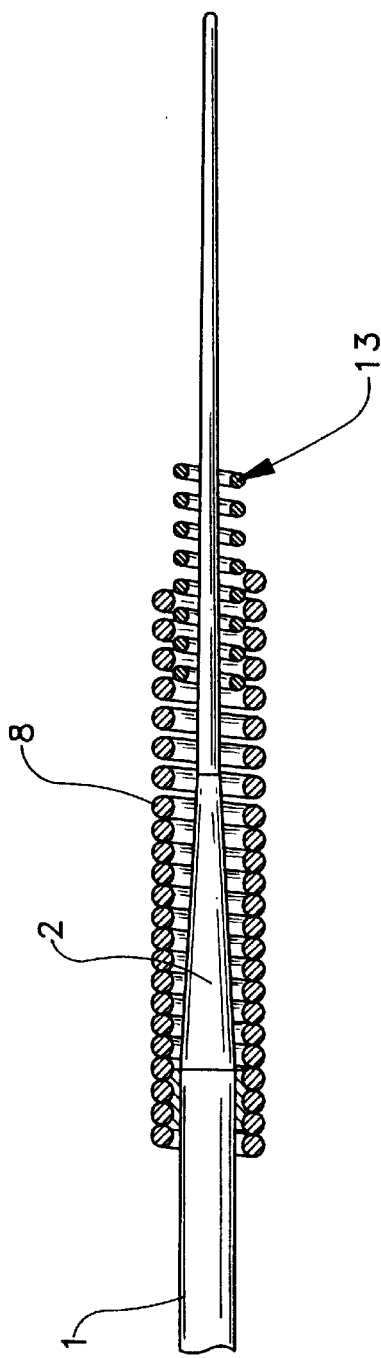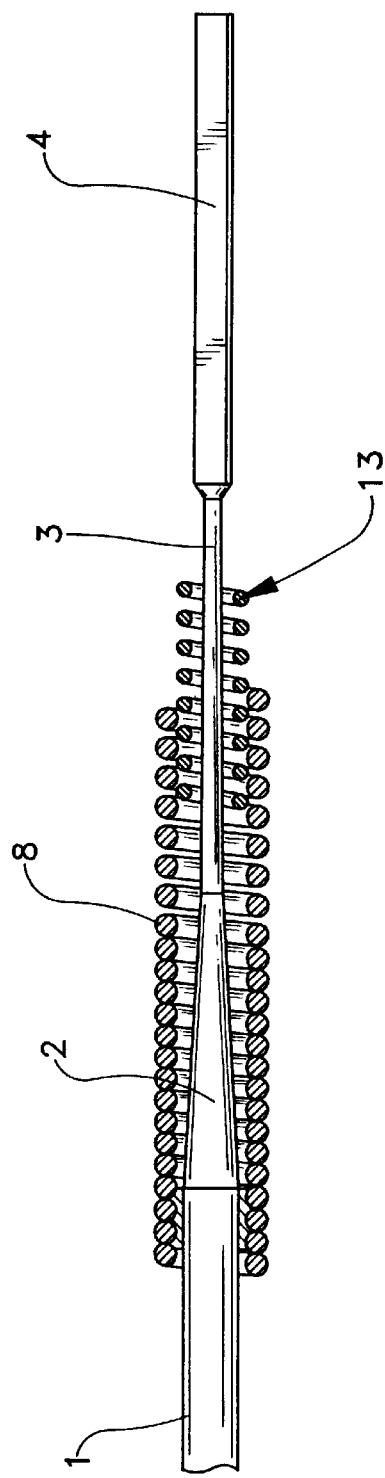
FIG-2c
FIG-2d

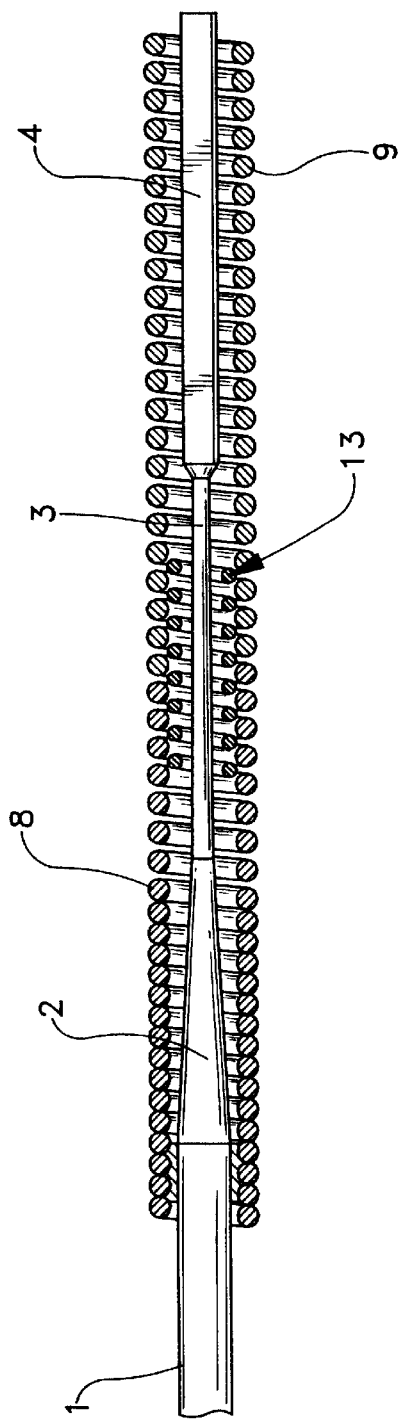
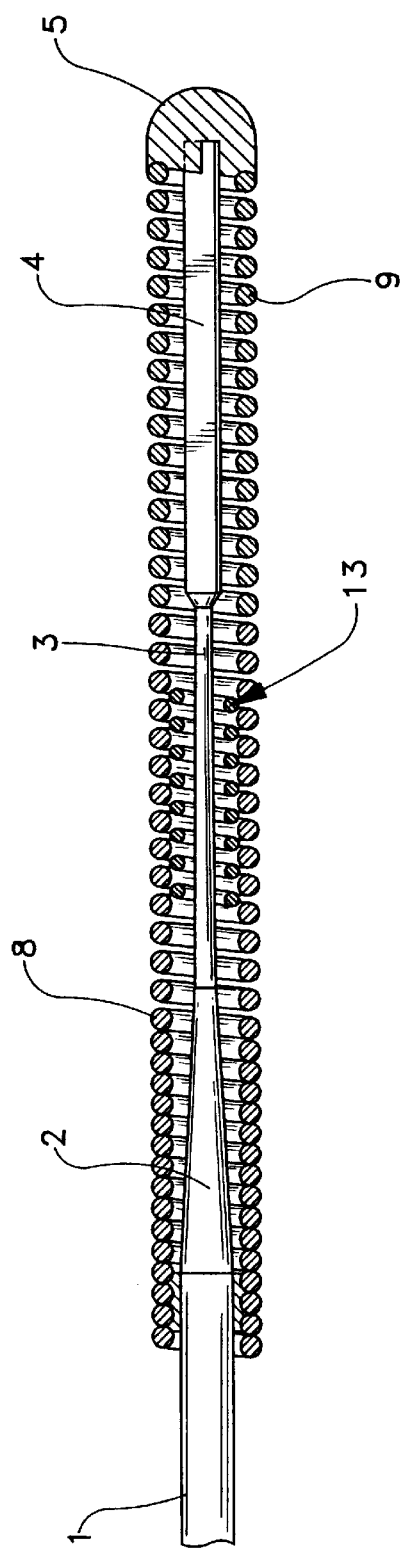

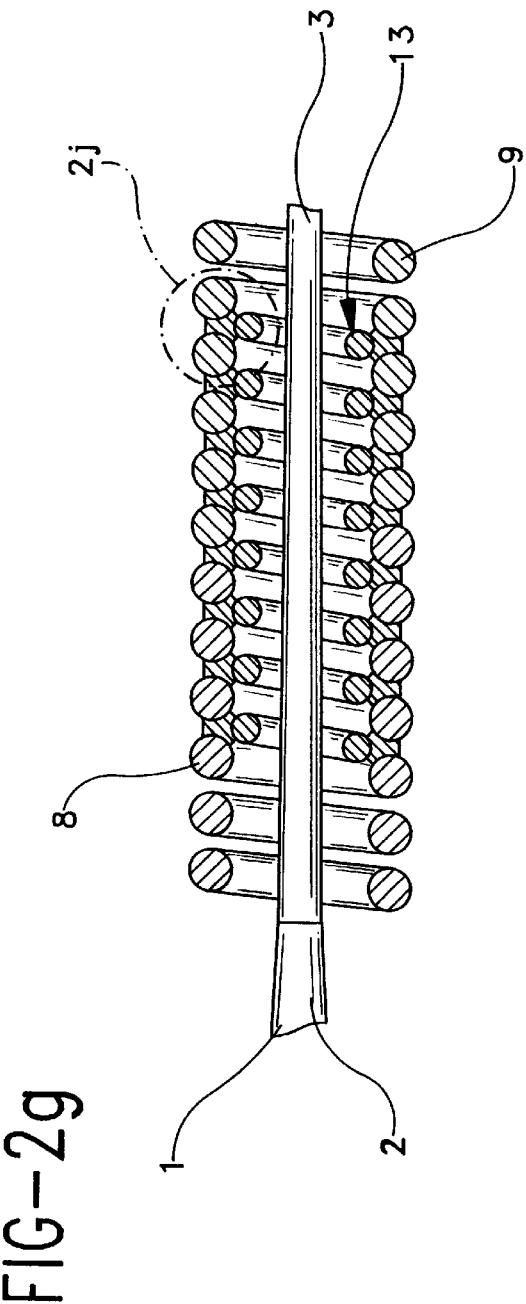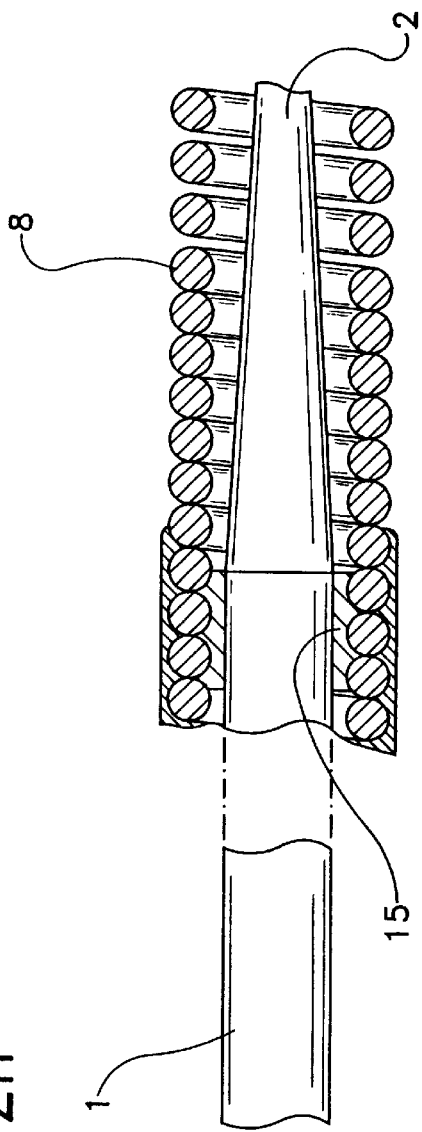
FIG-2g
FIG-2h

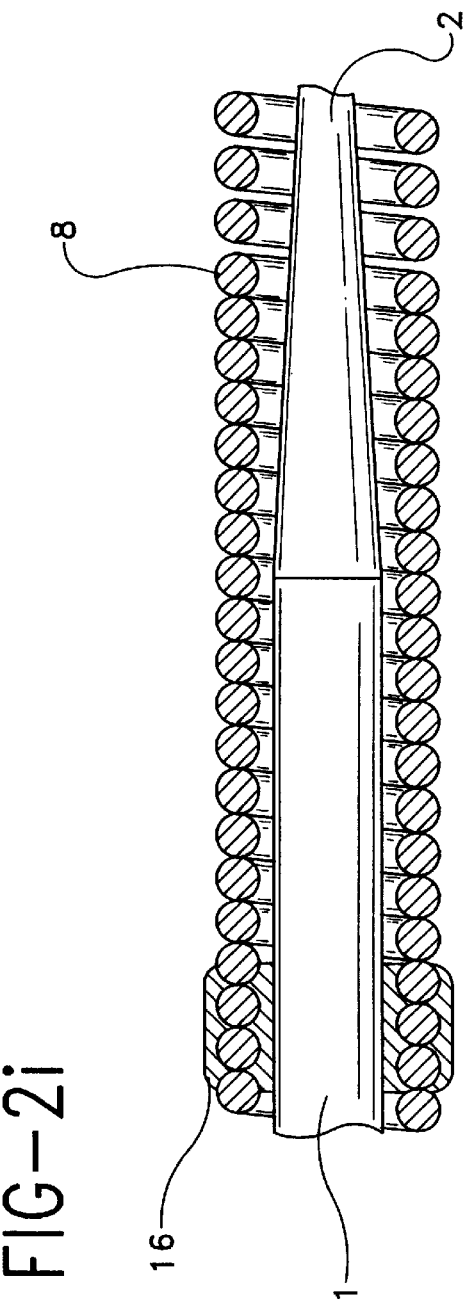
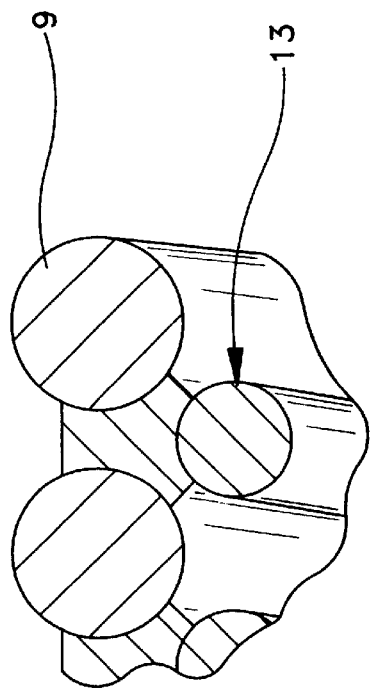

GUIDE WIRE

This is a continuation of application Ser. No. 08/207,576, filed on Mar. 7, 1994, now U.S. Pat No. 5,429,139.

BACKGROUND OF THE INVENTION

The invention pertains to a guide wire, especially for the percutaneous introduction of a balloon dilatation catheter into a blood vessel, with an elongated flexible shaft that contains a proximal end and a tapered distal end, and having a flexible spiral (helical coil) that surrounds the distal end of the shaft and is attached to it. The helical coil contains a distal radiographically visible part, a proximal radiographically invisible part and connection agents for the joining of the two parts of the helical coil.

Guide wires are known in several versions. For the introduction of a balloon catheter into a blood vessel, the guide wire is inserted into the blood vessel with the aid of a guide catheter, and the balloon catheter is pushed onto the guide wire and advanced in the vessel until the spot intended for treatment is reached. In the placement of the guide wire it is important that its distal end is steerable within the blood vessel and is visible on the-X-ray screen. Furthermore, it should also be possible to make the region of the blood vessel intended for treatment visible with the aid of a contrasting agent. To assure that the distal end of the guide wire has the smallest negative effect on the visibility of the vessel, with the guide wires of the known design only a frontal section of the helical coil is opaque to X-rays and, therefore, easily visible. The two parts of the helical coil have to be securely connected to each other, so that breakage of the helical coil during treatment can be eliminated. On the other hand, the connection of these two parts should not diminish the steerability and the flexibility of the guide wire.

In the guide wire according to U.S. Pat. No. 4,922,924, both parts of the helical coil are turned (screwed) into each other over several stretched turns (coils). At the ends of the bifilar section, both parts are soldered to each other and to the central shaft. A safety wire is inserted in the helical coil with one end connected to the shaft and the other end connected to the distal tip of the guide wire. This safety wire is intended to assure that the helical coil can be bent into a certain form and that in case of breakage of the helical coil the distal part of the helical coil cannot separate from the shaft.

U.S. Pat. No. 4,748,986 shows a similar guide wire, in which also a distal part of the helical coil is screwed into a proximal part and is soldered together with it and also with the shaft. The soldered area extends here over the entire bifilar section, and this guide wire is also provided with a safety wire that connects the tip with the shaft.

The critical points in these guide wires are each located at the proximal and distal ends of the bifilar section. There, the turns of the helical coil are separated by (a distance equal to) the wire diameter of the helical coil, so that the respective other helical coil can be screwed into it. This space between the coils is filled in the bifilar section by the opposing second helical coil. At a certain distance from the bifilar section, the space between the coils is again normalized to a smaller dimension. However, an area that is sensitive to buckling is created between the bifilar section and the helical coil where the space between the coils is normal, since the second helical coil is missing there, but the space between the coils is not yet normalized.

Another problem is created in the assembly of the helical coils. They have to be precisely positioned for screwing them together, and be held such that both helical coils are situated in the assembled state in perfect alignment and do combine after soldering to a smooth, stepless continuous guide wire.

WO 92/04072 describes a guide wire that at its distal end is provided with two helical coils in coaxial alignment to each other. Of these, a smaller inner helical coil is on one end soldered to the shaft. The other, larger helical coil is at the distal end soldered to a tip of the guide wire, and is at proximal portions soldered to the shaft and a proximal part of the inner helical coil. Guide wires with two coaxial helical coils are also known from U.S. Pat. No. 5,144,959 and U.S. Pat. No. 5,063,935. The inner helical coil is at the proximal end connected with the shaft, and at the distal end with the tip of the guide wire.

SUMMARY OF THE INVENTION

The invention is based on the objective to create a guide wire that has a helical coil assembly with an unchanged flexibility also in the area where the helical coils are connected together, and that is easier to manufacture, but nevertheless safe and easily steerable. The objective is reached in the generic guide wire by having the means of connection include a connecting helical coil that is screwed with one end into the proximal helical coil, and with the other end into the distal helical coil. The entire helical coil assembly composed of three helical coils, behaves in its flexibility essentially like a helical coil wound from a single wire. The relatively short X-ray-visible area is sharply distinguished. The two opposing ends of the proximal helical coil and the distal helical coil can in the guide wire according to the invention butt together. The mechanical properties and especially the flexibility of the helical coil assembly are in the guide wire according to the invention also in the area of the connection point of the proximal helical coil and the distal helical coil essentially uniform over the entire length of the helical coil assembly, so that the connection point does, therefore, not impair the steerability of the guide wire. Furthermore, the outside of the helical coil assembly is essentially uniform over its entire length and the coils are automatically centered during assembly. Additional advantageous characteristics of the invention result from the dependent claims, the following description, and the drawing.

BRIEF DESCRIPTION OF THE DRAWINGS

An example of execution of the invention is described further in the following drawings. Depicted are in:

FIG. 1a in greatly enlarged scale a view of a partly longitudinal section of a guide wire according to the invention, FIG. 1b a partial view of the guide wire according to FIG. 1a, and FIGS. 2a to 2j schematic depictions of the distal end of the guide wire for elucidation of the process for its manufacture.

DETAILED DESCRIPTION OF THE INVENTION

Figure 2A:
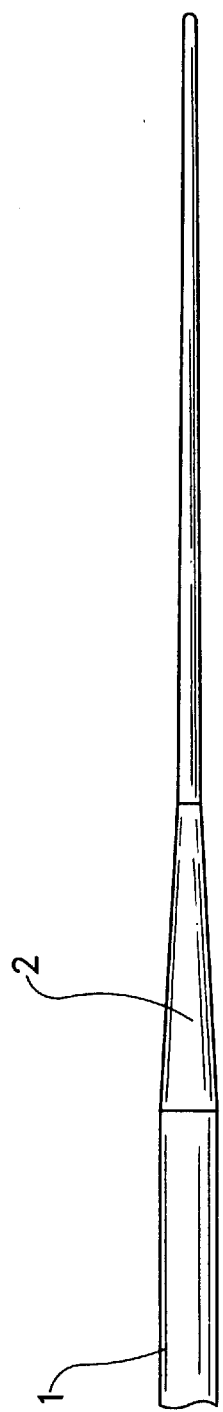

The guide wire contains a helical coil assembly spring 6 that is pushed onto the distal end of a shaft 1, and which on this shaft 1 is connected to the shaft 1 at the distal end by a tip 5 that is rounded in front, and at the proximal end by a soldered point 16. The total length of the guide wire or the shaft 1 is, e.g., 175 cm, while the length of the helical coil assembly 6 is, e.g., approximately 30 cm.

The wire-like Teflon®-coated shaft 1 has proximally of a conically tapered zone 2 a circular cross section with a diameter of approximately 0.15 mm. Between the conically tapered zone 2 and a flattened distal zone 4, the shaft 1 has in a zone 3 also a uniform circular cross section, with a diameter of, e.g., 0.075 mm. In zone 4, the shaft is, e.g., over a length of approximately 2 cm flattened to a thickness of, e.g., 0.05 mm. The torsion transfer is increased by the flattening of the shaft 1 at its distal end, and the danger of fatigue is simultaneously reduced.

The guide wire is provided on its outside, with the exception of a zone 17, in a generally known way with a Teflon® coating 7. This coating reduces the friction of the guide wire, if it is moved within a guide catheter of generally known design, not shown here.

The helical coil assembly spring 6 consists of a proximal helical coil 8 and a distal helical coil 9, which are permanently connected to each other by a connecting helical coil 13. The proximal helical coil 8 is wound from a non-corroding flexible steel wire 18 with a diameter of approximately 0.075 mm, and subsequently coated with Teflon® or another slippery plastic. In a zone 10 of approximately eight to ten coils, proximal helical coil 8, as visible in FIG. 1a is somewhat stretched so that the described coils are here only slightly opened. The distal helical coil 9 is wound from a gold-coated tungsten wire of approximately 0.075 mm thickness in an outside dimension of approximately 0.35 mm. This distal helical coil 9 is on its outside advantageously not coated with Teflon®. Distal helical coil 9 is in its entire length, over all coils, slightly opened, in order to increase the flexibility of distal helical coil 9.

The connecting helical coil 13 is screwed with one end into the inside of proximal helical coil 8, and with the other end also into the inside of distal helical coil 9. The connecting helical coil 13 has, e.g., eight coils that similar to a thread do insert into proximal helical coil 8 and distal helical coil 9. The connecting helical coil 13 is manufactured on a winding spindle with an outside diameter of 0.1 mm from a gold-coated tungsten wire with an outside diameter of approximately 0.05 mm. It too, is in the longitudinal direction somewhat stretched. The connecting helical coil 13 is preferentially over its entire length solidly connected to proximal helical coil 8 and distal helical coil 9 with silver solder. Distal helical coil 9 and the connecting helical coil are easily visible in radiography, especially also due to the material concentration by connecting helical coil 13, while, in contrast to it, the proximal helical coil 8 is radiographically invisible. Therefore, distal helical coil 9 can be radiographically observed during the introduction of the distal tip of the guide wire. It is essential that the flexibility of the helical coil assembly 6 is not significantly impaired by the connecting helical coil 13 and its soldering with proximal helical coil 8 and distal helical coil 9. Helical coil assembly 6 has, therefore, in its flexibility similar properties as a non-assembled helical coil. As depicted in FIG. 1b, the ends 8a and 9a of the proximal helical coils 8 and distal helical coil 9 are butt-joined so that the two wires forming the proximal helical coil 8 and the distal helical coil 9 run stepless into each other and the outside diameter of the entire helical coil assembly 6 is uniform.

The manufacture of the guide wire according to the invention is in the following briefly described with the aid of FIGS. 2a to 2i.

Figure 2B:
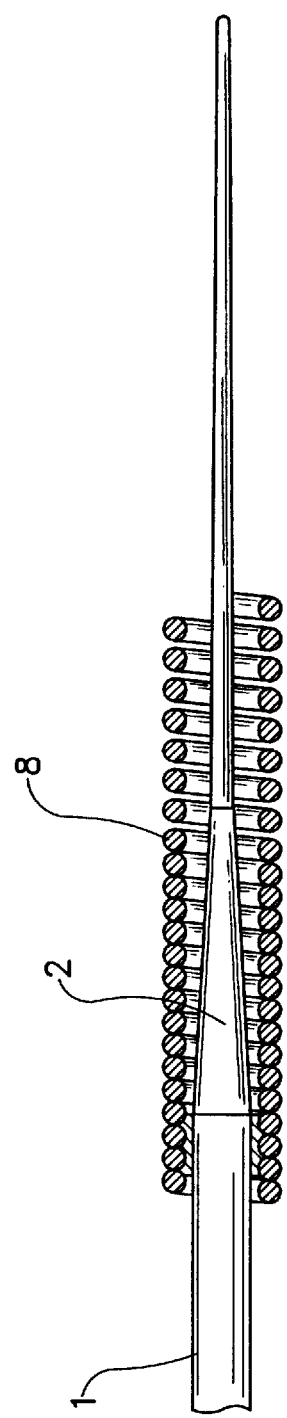

According to FIGS. 2a and 2b, proximal helical coil 8 is pushed from the distal end onto the shaft 1, and the connecting helical coil 13 with, e.g., four coils, is screwed into the distal end of proximal helical coil 8. The circular tip of shaft 1 is now flattened and obtains approximately the shape shown in FIG. 2d. In the next process step, the distal helical coil 9 is pushed onto the shaft 1 and screwed onto the connecting helical coil 13. FIG. 2e. Distal helical coil 9 is solidly connected to shaft 1 by plasma jet welding or soldering of the distal tip, and the tip 5 created thereby is frontally rounded off. FIG. 2f. Then, the connecting helical coil 13 is soldered together with the proximal helical coil 8 and distal helical coil 9. As shown in FIG. 2g, the soldering point 14 essentially extends over the entire length of the connecting helical coil 13. According to FIG. 2h, an adhesive point 15 is provided that connects shaft 1 with proximal helical coil 8, for the purpose of improving the torsion transfer. Finally, proximal helical coil 8 is at its proximal end soldered to shaft 1 so that the soldering point 16, shown in FIG. 2i, is created. This soldering point 16 is preferentially created last, so that the helical coil assembly 6 lies absolutely stress-free over shaft 1.

I claim:

1. A guide wire comprising:

an elongated flexible shaft with a proximal portion and a distal portion, a helical coil assembly connected to the distal portion of the shaft, the helical coil assembly including a distal helical coil and a proximal helical coil; and a connecting helical coil adapted to make longitudinally overlapping contact with both the distal and proximal helical coils to connect the distal helical coil to the proximal helical coil;

wherein the distal, proximal, and connecting helical coils each comprise an element having a circular cross-section.

2. The guide wire according to claim 1 where the coils in the connecting helical coil are spaced apart in the longitudinal direction.

3. The guide wire according to claim 2 where the distal end of the proximal helical coil is butt joined to the proximal end of the distal helical coil.

4. The guide wire according to claim 3 where the connecting helical coil is formed from six to eight coils.

5. The guide wire according to claim 4 where the wire has an outside diameter of 0.05 to 0.10 mm.

6. The guide wire according to claim 5 where the connecting helical coil is soldered to the proximal helical coil and to the distal helical coil.

7. The guide wire according to claim 6 where the connecting helical coil is soldered along its outside to the proximal helical coil and to the distal helical coil.

8. The guide wire according to claim 7 where the shaft has a distal tip that is rigidly attached to the helical coil assembly by a plasma jet welding point.

9. The guide wire according to claim 8 where the proximal helical coil is attached to the shaft through an adhesive point.

10. The guide wire according to claim 9 where the proximal helical coil is made from a non-corroding steel wire.

11. The guide wire according to claim 10 where the outside diameter of the proximal helical coil is substantially the same as the outside diameter of the distal helical coil.

12. A guide wire comprising:

an elongated flexible shaft with a proximal portion and a distal portion, a helical coil assembly connected to the distal portion of the shaft, the helical coil assembly including a distal helical coil and a proximal helical coil;

a connecting helical coil adapted to make longitudinally overlapping contact with both the distal and proximal helical coils to connect the distal helical coil to the proximal helical coil; and marking means comprising a radiographically visible marker on or in the distal portion of the guide wire;

wherein the distal, proximal, and connecting helical coils each comprise an element having a circular cross-section.

13. The guide wire according to claim 12 where the coils in the connecting helical coil are spaced apart in the longitudinal direction.

14. The guide wire according to claim 13 where the distal end of the proximal helical coil is butt joined to the proximal end of the distal helical coil.

15. The guide wire according to claim 14 where the connecting helical coil is formed from six to eight coils.

16. The guide wire according to claim 15 where the wire has an outside diameter of 0.05 to 0.10 mm.

17. The guide wire according to claim 16 where the connecting helical coil is soldered to the proximal helical coil and to the distal helical coil.

18. The guide wire according to claim 17 where the connecting helical coil is soldered along its outside to the proximal helical coil and to the distal helical coil.

19. The guide wire according to claim 18 where the shaft has a distal tip that is rigidly attached to the helical coil assembly by a plasma jet welding point.

20. The guide wire according to claim 19 where the proximal helical coil is attached to the shaft through an adhesive point.

21. The guide wire according to claim 20 where the proximal helical coil is made from a non-corroding steel wire.

22. The guide wire according to claim 21 where the outside diameter of the proximal helical coil is substantially the same as the outside diameter of the distal helical coil.

23. A guide wire comprising:

an elongated flexible shaft with a proximal portion and a distal portion, a helical coil assembly connected to the distal portion of the shaft, the helical coil assembly including a distal helical coil and a proximal helical coil; and a connecting helical coil adapted to make contact with the distal and proximal helical coils and to connect the distal helical coil to the proximal helical coil, the connecting helical coil having one end screwed into a distal portion of the proximal helical coil and another end screwed into a proximal portion of the distal helical coil.

24. A guide wire comprising:

an elongated flexible shaft with a proximal portion and a distal portion, a helical coil assembly connected to the distal portion of the shaft, the helical coil assembly including a distal helical coil and a proximal helical coil; and a connecting helical coil adapted to make contact with the distal and proximal helical coils and to connect the distal helical coil to the proximal helical coil;

wherein the coils in the distal portion of the proximal helical coil and the coils in the proximal portion of the distal helical coil are spaced apart in the longitudinal direction to create slots between adjacent coils having a longitudinal dimension smaller than the wire diameter of the connecting helical coil.

25. A guide wire comprising:

an elongated flexible shaft with a proximal portion and a distal portion, a helical coil assembly connected to the distal portion of the shaft, the helical coil assembly including a distal helical coil and a proximal helical coil;

a connecting helical coil adapted to make contact with the distal and proximal helical coils and to connect the distal helical coil to the proximal helical coil, the connecting helical coil having one end screwed into a distal portion of the proximal helical coil and another end screwed into a proximal portion of the distal helical coil; and marking means comprising a radiographically visible marker on or in the distal portion of the guide wire.

26. A guide wire comprising:

an elongated flexible shaft with a proximal portion and a distal portion, a helical coil assembly connected to the distal portion of the shaft, the helical coil assembly including a distal helical coil and a proximal helical coil;

a connecting helical coil adapted to make contact with the distal and proximal helical coils and to connect the distal helical coil to the proximal helical coil; and marking means comprising a radiographically visible marker on or in the distal portion of the guide wire;

wherein the coils in the distal portion of the proximal helical coil and the coils in the proximal portion of the distal helical coil are spaced apart in the longitudinal direction to create slots between adjacent coils having a longitudinal dimension smaller than the wire diameter of the connecting helical coil.

* * * * *